US008362304B2

(12) United States Patent
Fadakar et al.

(10) Patent No.: US 8,362,304 B2
(45) Date of Patent: Jan. 29, 2013

(54) PROCESS FOR MAKING GLYCOL ETHER COMPOSITIONS USEFUL FOR METAL RECOVERY

(75) Inventors: Farhad Fadakar, Downingtown, PA (US); Adam Chan, West Chester, PA (US)

(73) Assignee: Lyondell Chemical Technology, L.P., Houston, TX (US)

( * ) Notice: Subject to any disclaimer, the term of this patent is extended or adjusted under 35 U.S.C. 154(b) by 710 days.

(21) Appl. No.: 12/460,225

(22) Filed: Jul. 15, 2009

(65) Prior Publication Data

US 2011/0011210 A1 Jan. 20, 2011

(51) Int. Cl.

| | |
|---|---|
| ***C07C 41/03*** | (2006.01) |
| ***C07C 43/13*** | (2006.01) |
| *C22B 15/00* | (2006.01) |
| *C22B 11/10* | (2006.01) |
| *B03D 1/008* | (2006.01) |

(52) U.S. Cl. ........ 568/618; 568/621; 568/622; 568/623; 252/61

(58) Field of Classification Search ........................ None
See application file for complete search history.

(56) References Cited

U.S. PATENT DOCUMENTS

| | | | | |
|---|---|---|---|---|
| 2,611,485 | A | 4/1949 | Tveter | |
| 2,695,101 | A | 11/1954 | Booth et al. | |
| 3,595,390 | A | 7/1971 | Booth | |
| 3,829,505 | A | 8/1974 | Herold | |
| 4,929,344 | A | 5/1990 | Fleming | |
| 5,158,922 | A | 10/1992 | Hinney et al. | |
| 5,232,581 | A | 8/1993 | Roberts et al. | |
| 5,470,813 | A | 11/1995 | Le-Khac | |
| 5,482,908 | A | 1/1996 | Le-Khac | |
| 7,482,495 | B2 | 1/2009 | Fadakar | |
| 2007/0149825 | A1 * | 6/2007 | Fadakar | 568/679 |

* cited by examiner

*Primary Examiner* — Rosalynd Keys

(57) ABSTRACT

Glycol ether compositions useful for metal recovery by froth flotation and processes for making the compositions are disclosed. In one process, dipropylene glycol methyl ether (DPM) is propoxylated to give a composition comprising 4 to 15 wt. % of DPM and at least 20 wt. % of tripropylene glycol methyl ether (TPM). In another process, the glycol ether composition is made from a distillation residue which comprises DPM, TPM, and a basic catalyst. Extraction of the residue with water to remove some of the basic catalyst is followed by propoxylated to give a composition which comprises less than 15 wt. % of DPM, at least 20 wt. % of TPM, and one or more PO-based glycols. In comparative froth tests, glycol ether compositions of the invention meet or exceed the performance of commercial frothers.

9 Claims, No Drawings

PROCESS FOR MAKING GLYCOL ETHER COMPOSITIONS USEFUL FOR METAL RECOVERY

FIELD OF THE INVENTION

The invention relates to a process for making glycol ether compositions useful for mining applications.

BACKGROUND OF THE INVENTION

Froth flotation is commonly used in the mining industry to recover mineral values from aqueous ore slurries. A wide variety of suitable frothing agents ("frothers") have been identified, although the best frother for a particular application is usually selected through experience or by trial and error. Alkyl or aryl ethers of propylene glycol and polypropylene glycols have long been generally known as effective frothers for copper recovery (see, e.g., U.S. Pat. Nos. 2,611,485, 2,695,101, and 3,595,390).

The South African mining industry uses tripropylene glycol methyl ether (TPM) as a component of frothers for recovering platinum and other precious metals. While the product performs well, it is produced commercially as a by-product of the normal process for making propylene glycol methyl ether (PM) from methanol and propylene oxide. Usually, TPM is recovered after a labor-intensive series of steps that includes base-catalyzed alkoxylation, distillations to recover PM and dipropylene glycol methyl ether (DPM), water extraction of the distillation residue (known as "DPM column bottoms") to remove the basic catalyst, and multiple distillations to recover purified DPM and TPM. Consequently, TPM is expensive and in relatively short supply. Unfortunately, demand for TPM is still not sufficient to justify its "on purpose" manufacture.

The mining industry, particularly the platinum mining industry, would benefit from the availability of inexpensive alternatives to TPM that provide acceptable performance as frothers. Not all glycol ether compositions are suitable for use in platinum recovery. For example, our own evaluation of ethoxylated PM demonstrated unacceptable frothing performance.

Recently, we described (U.S. Pat. No. 7,482,495) a way to make glycol ether compositions that are useful for metal recovery. Reaction of PM with from 1.5 to 3 equivalents of propylene oxide (PO) provides an initial alkoxylation mixture that is generally unsuitable for use as a frother. Distillation of this material, however, to remove some of the DPM affords a composition comprising at least 30 wt. % of TPM and less than 20 wt. % of DPM, and this distilled product performs well in tests designed to predict performance in frother applications. Moreover, similar results can be achieved by reacting DPM with from 0.5 to 1.5 equivalents of PO, followed by distillation, to make an analogous product.

Despite the success of the compositions of the '495 patent and their advantages over highly purified materials such as TPM, there is room for improvement. The fractional distillation used to reduce the DPM level is cumbersome and requires diligent sampling and analysis to ensure that the product will meet targeted specifications. A single batch of off-spec material can trigger substantial process tweaking and product blending to generate a finished product that meets specifications. Moreover, distilling and recycling DPM is energy-intensive and unproductive; the need to recycle DPM reduces batch yields by 20% or more. Preferably, the process would avoid the need for a distillation step.

Thus, a valuable process would overcome the need to: (1) start with relatively pure PM or DPM (each of which is obtained after multiple distillations); (2) add an alkoxylation catalyst; or (3) perform multiple distillations to purify the alkoxylated product.

Finally, better frothers are always desirable. The best frothers generate a stable froth when an ore-containing liquid mixture is aerated in the presence of a small proportion of frother. Metal values are recovered by separating the froth from the bulk of the liquid mixture. A valuable frother provides a froth of limited stability such that removal of aeration results in rapid collapse of the froth and permits easy isolation of the metal components. An ideal process would provide frothers that meet or exceed the performance of commercial frothers, including TPM.

SUMMARY OF THE INVENTION

The invention relates to processes for making glycol ether compositions. In one process, dipropylene glycol methyl ether (DPM) reacts with 1.8 to 2.5 equivalents of propylene oxide (PO) in the presence of an alkoxylation catalyst. The resulting glycol ether composition comprises 4 to 15 wt. % of DPM and at least 20 wt. % of tripropylene glycol methyl ether (TPM).

In another process of the invention, the glycol ether composition is made from a distillation residue which comprises DPM, TPM, and at least 5 wt. % of a basic catalyst. In this process, the residue is extracted with water to remove some of the basic catalyst. The extraction provides an extracted residue that comprises DPM, TPM, less than 15 wt. % water, and less than 1 wt. % of the basic catalyst. The extracted residue then reacts with propylene oxide in an amount effective to give a glycol ether composition which comprises 4 to 15 wt. % of DPM, at least 20 wt. % of TPM, and one or more PO-based glycols. This composition is useful "as is" for frothing.

The invention includes glycol ether compositions made by the processes and their use in froth flotation for metal recovery from metallic ores. In comparative froth tests, glycol ether compositions of the invention meet or exceed the performance of commercial frothers.

DETAILED DESCRIPTION OF THE INVENTION

The invention relates to processes useful for making glycol ether compositions that are valuable for mining applications, particularly metal recovery by froth flotation.

In one process of the invention, dipropylene glycol methyl ether (DPM) reacts with 1.8 to 2.5 equivalents of propylene oxide in the presence of an alkoxylation catalyst.

DPM suitable for use is one or more of four possible isomers of dipropylene glycol methyl ether. The most common isomer is the secondary alcohol resulting from the reaction of "PM-1" (1-methoxy-2-propanol) with propylene oxide (1-methoxy-2-propanol, 2-hydroxypropyl ether), but any combination of isomers can be used. DPM is commercially available from Lyondell Chemical Company as ARCOSOLV® DPM.

DPM used in the inventive process can be prepared by the base-catalyzed reaction of methanol and about two equivalents of propylene oxide (PO), followed by distillation. DPM can also be made by reacting propylene glycol methyl ether (PM) with about one equivalent of PO in the presence of base. The source and purity level of the DPM is usually not critical. Thus, a mixture comprising mostly DPM that also contains other glycol ethers (PM, TPM, etc.) can be used instead of pure DPM. For example, a mixture comprising 80 wt. % DPM, 10 wt. % PM, and 10 wt. % TPM is suitable for use.

The DPM reacts with 1.8 to 2.5 equivalents of propylene oxide. Preferably, propylene oxide is used in an amount within the range of 1.9 to 2.1 equivalents. If too little PO is used, the DPM level in the glycol ether composition exceeds 15 wt. % and/or the TPM level fails to reach at least 20 wt. %, resulting in inferior frothing performance. If too much PO is used, the amount of DPM in the glycol ether composition falls below 4 wt. %, which either produces an inferior product or uses more PO than is necessary to achieve the desired result.

An alkoxylation catalyst is used. The type of catalyst used is not critical. Suitable catalysts include alkali metals, alkali metal hydroxides, alkali metal alkoxides, and the like. Potassium hydroxide and sodium hydroxide are particularly preferred. Suitable catalysts also include double metal cyanide catalysts of the type described, for example, in U.S. Pat. Nos. 3,829,505, 5,158,922, 5,470,813, and 5,482,908, the teachings of which are incorporated herein by reference.

The reaction of DPM and 1.8 to 2.5 equivalents of PO is performed under conditions effective to produce a glycol ether composition comprising 4 to 15 wt. % of DPM and at least 20 wt. % of tripropylene glycol methyl ether (TPM). The mixture normally includes DPM, TPM, and higher DPM propoxylates, and may include other components. We surprisingly found that unlike earlier glycol ether mixtures (such as those described in U.S. Pat. No. 7,482,495), this one need not be distilled to remove volatile components to render it suitable for use in froth flotation. Even without further processing, these compositions provide acceptable results in qualitative tests designed to approximate good performance in the field for recovering metals from ores by froth flotation.

One of these tests ("froth stability") measures whether a stable froth can be generated at all with a particular frother; longer times indicate greater stability. A second test ("froth breakdown") measures how easily recovered metals can be separated cleanly from an isolated froth.

If desired, the alkoxylation catalyst can be removed from the glycol ether composition. For example, the composition can be neutralized and filtered or it can be treated with an adsorbant such as magnesium silicate to remove the alkoxylation catalyst. When a basic alkoxylation catalyst is used, it is often removed. Ideally, however, the catalyst is not removed and the glycol ether composition is simply used "as is" in the frother application.

This process of the invention is illustrated by the preparation of Frother A, below. Results of froth testing appear in Example 1 and Comparative Examples 2-4 (see Table 1). The examples demonstrate that the inventive process provides glycol ether compositions that are easy to prepare, yet they rival or better the performance of commercial benchmarks. Frother B provides similar performance but requires a distillation step in its preparation to reduce the level of DPM to a suitable concentration.

In a second process of the invention, the glycol ether composition is made from a distillation residue. This residue, known as "DPM column bottoms" or more simply "DPM bottoms," comprises DPM, TPM, and at least 5 wt. % of a basic catalyst. DPM bottoms is readily available as the residue from a distillation column in which DPM is recovered as the principal product. This is usually the second distillation in an overall process for making PM and DPM from a base-catalyzed reaction of methanol and propylene oxide. After PM is recovered by distillation, the less-volatile material is distilled to recover DPM. The residue from this second distillation is "DPM bottoms." DPM bottoms typically contains about 40-50 wt. % DPM, 40-50 wt. % TPM, 5-20 wt. % of a basic catalyst, and other minor components.

The residue is first extracted with water to remove most of the basic catalyst. Before extraction, DPM bottoms preferably contains 8-12 wt. % of the basic catalyst. Enough water is used to reduce the catalyst level in the residue to less than 1 wt. %. The amount of water used is usually limited, however, to avoid losing too much of the organic phase in the aqueous phase. Typically, the weight ratio of water to residue is within the range of 1:1 to 1:5, preferably within the range of 1:2 to 1:4. After extraction with water, the organic phase comprises DPM, TPM, less than 15 wt. % of water, and less than 1 wt. % of the basic catalyst.

The water-extracted residue is then reacted with propylene oxide. PO is used in an amount effective to produce a glycol ether composition comprising 4 to 15 wt. % of DPM, at least 20 wt. % of TPM, and one or more PO-based glycols. The composition also includes the basic catalyst. The PO-based glycols (propylene glycol, dipropylene glycol, tripropylene glycol, etc.) result from propoxylation of water and are preferably present in the glycol ether composition at a level within the range of 2 to 12 wt. %; preferably, tripropylene glycol is the predominant PO-based glycol.

Usually, the PO and the extracted residue are reacted such that the weight ratio of PO to residue is within the range of 0.6 to 1.0, more preferably from 0.7 to 0.9, and most preferably about 0.8. The propoxylation reaction can be performed over a wide temperature range, but it is preferably performed at temperatures in the range of 50° C. to 200° C. Propoxylation reduces the DPM content of the mixture to 4-15 wt. % and increases the TPM content to at least 20 wt. %. As noted earlier, the catalyst can be removed at this point if desired, but it is preferably left in the glycol ether composition, which can then be used "as is" as part of a formulation for froth flotation.

This process of the invention is illustrated by the preparation of Frother E, below. Results of froth testing appear in Example 5 and Comparative Examples 6-9 (see Table 2). The examples demonstrate that the inventive process provides glycol ether compositions that are easy to prepare from a crude starting material, yet they rival or better the performance of commercial benchmarks. Moreover, the presence of PO-based glycols in the mixtures does not appear detrimental to frother performance. Frother B provides comparable performance but requires a distillation step in its preparation to reduce the level of DPM to a suitable concentration.

Overall, the inventive processes provide effective products for use in metal recovery from metallic ores. Compared with TPM, the alkoxylated glycol ether compositions of the invention are cheaper and require less purification. On the other hand, the performance of the glycol ether compositions rivals or exceeds those of TPM or other polyether frother compositions.

The invention includes glycol ether compositions made by the processes of the invention. The glycol ethers are useful as frothers for recovering metals and other mineral values from metallic ores generated in mining operations, especially platinum or copper. In another aspect, the invention includes a froth flotation method which comprises recovering a metal, preferably platinum or copper, from a metallic ore in the presence of a frother comprising a glycol ether composition of the invention.

In a typical froth flotation method, the metallic ore is crushed and wet ground to obtain a "pulp." The frother, usually employed with a collector, is added to the ore to assist in separating valuable minerals from the undesired portions of the ore in subsequent flotation steps. The pulp is aerated to produce a froth at the liquid surface. The collector assists the frother in separating the mineral values from the ore by causing the mineral values to adhere to the bubbles formed during aeration. Adherence is selective; the portion of the ore not containing mineral values does not adhere to the bubbles. The mineral-bearing froth is collected and further processed to obtain the desired minerals. For more details of how to use frothers to recover metal values by froth flotation, see U.S. Pat. Nos. 2,611,485, 2,695,101, 3,595,390, 4,929,344, and 5,232,581, the teachings of which are incorporated herein by reference.

The following examples merely illustrate the invention. Those skilled in the art will recognize many variations that are within the spirit of the invention and scope of the claims.

EXAMPLE A

Preparation of Frother A: Propoxylation of DPM

A reactor is charged with dipropylene glycol methyl ether ("DPM," 2800 g, 19 mol). Potassium hydroxide flakes (15 g) are stirred into the DPM, and the mixture is heated to about 140° C. Propylene oxide (a total of 2200 g, 38 mol) is added slowly at first to the stirred mixture until an exotherm indicates commencement of propoxylation. The PO addition rate is then increased slowly to the maximum desirable rate. The reaction temperature is maintained at about 140° C., and the addition is complete within 1 h. Following PO addition, the reaction mixture is held at about 140° C. for 3 h to consume residual PO. The reactor contents are cooled (50-60° C.) and neutralized (to pH=7) with glacial acetic acid. Analysis of the product by gas chromatography shows a final DPM concentration of about 8 wt. % and a TPM concentration of about 23 wt. %. This product is used without further purification as "Frother A."

COMPARATIVE EXAMPLE B

Preparation of Frother B: Distillation Included

The procedure of U.S. Pat. No. 7,482,495, Example 2 is generally followed to react dipropylene glycol methyl ether (DPM) with propylene oxide. Vacuum distillation is then used to remove volatile compounds and reduce the DPM concentration to about 12 wt. % The product, which contains about 42 wt. % of tripropylene glycol methyl ether (TPM), is cooled and neutralized as described earlier.

Froth Test

Frother A is compared with Frother B and two commercial frothers (C and D). Frother C is DowFroth™ 250, a product of Dow Chemical. Frother D is tripropylene glycol methyl ether. Testing is performed using platinum ore samples that are ground to either a coarse or fine powder prior to use. For each sample, froth stability and froth breakdown are evaluated.

1. Froth Stability.

"Froth stability" is the tendency of a frother composition to support the formation of a stable froth upon sustained air injection. Each frother is tested using both coarsely and finely ground ores at six dosing rates ranging from 10 to 320 g per ton equivalent of ore sample. A froth is produced by injecting air into a mixture containing the requisite amounts of ore particles, water, and frother. The resulting froth rises in a graduated vessel, and the maximum heights (in mm) of a stable froth are compared. Curves of stable froth height versus frother dose are compared. Based on the performance of each frother at the six different dosage levels, the tested frothers are ranked (1=highest froth height, 2=second highest, etc.).

2. Froth Breakdown.

"Froth breakdown" is a measure of the time needed for a stable, frothed composition to break down upon removal of air injection. Froth stability is first measured as described above. As part of the same test, air flow is discontinued, and the time needed for the froth to completely collapse (in seconds) is measured. Based on the performance of each frother at the six different dosage levels, the tested frothers are ranked (1=fastest breakdown; 2=second fastest, etc.).

Overall performance rank for each frother is computed by giving equal weight to each result and summing the four ranks obtained from the froth stability and froth breakdown tests for each grade of ore. The "score" is ideally 4 (i.e., four first-place ranks), and thus low score (as in golf) wins. Each frother in the series is then given an overall performance rank based on scores.

Results for Frother A and the comparative frothers appear in Table 1.

TABLE 1

Froth Test Results: Frother A versus Comparative Frothers

| | | Froth stabililty[1] ranking | | Froth breakdown[2] ranking | | | Overall |
|---|---|---|---|---|---|---|---|
| Ex. # | Frother | Coarse | Fine | Coarse | Fine | Score | rank |
| 1 | A | 3 | 1 | 1 | 3 | 8 | 1 |
| C2 | B | 2 | 3 | 2 | 2 | 9 | 2 |
| C3 | C | 1 | 2 | 3 | 4 | 10 | 3 |
| C4 | D | 4 | 4 | 4 | 1 | 13 | 4 |

Frothers:
A = frother made as in Ex. A;
B = frother made as in Comp. Ex. B;
C = DowFroth 250;
D = TPM
[1]Froth stability: measures whether a stable froth can be generated (more stable is higher rank)
[2]Froth breakdown: measures how easily the froth separates from the ore (faster is higher rank)

As shown in Table 1, Frother A outperforms commercial frothers C and D. Frother A's overall performance is slightly better than that of Frother B, which is made by the procedure of U.S. Pat. No. 7,482,495. Note that while performance is similar, Frother B requires a vacuum distillation step to reduce the DPM level while Frother A is conveniently prepared without the need for such a distillation.

EXAMPLE E

Preparation of Frother E from DPM Bottoms (5 wt. % DPM)

"DPM bottoms," a residue obtained from the PM manufacturing process that contains 40-50 wt. % DPM, 40-50 wt. % TPM, 3 wt. % of high-boiling component, and 8-10 wt. % of sodium methoxide catalyst, is used as a starting material to make Frother E. Thus, a sample of DPM bottoms is extracted with water (3:1 weight ratio of DPM bottoms to water) to remove most of the sodium methoxide catalyst from the DPM bottoms sample. After the water washing is complete, the extracted residue contains about 1 wt. % sodium methoxide and less than 15 wt. % water. This mixture is then reacted with propylene oxide without additional catalyst at a PO to residue weight ratio of about 0.8. Propoxylation reduces the DPM content of the mixture to about 5 wt. %. The mixture contains about 20 wt. % TPM. In addition to the propylene glycol ethers, the frother contains one or more PO-based glycols, which result from propoxylation of water.

COMPARATIVE EXAMPLE F

Preparation of Frother F from DPM Bottoms (17 wt. % DPM)

The procedure of Example E is repeated, except that the amount of propylene oxide reacted with the water-extracted bottoms sample is reduced to provide a PO to residue weight ratio of about 0.3. Propoxylation reduces the DPM content of the mixture to about 17 wt. %. The mixture contains about 46 wt. % TPM. The frother contains a mixture of the propylene glycol ethers and one or more PO-based glycols.

Froth Test

The performance of Frother E is compared with that of Frother B, Frother F, and commercial frothers C and D in the froth stability and froth breakdown experiments described earlier (see Table 2). Frother E is made by propoxylating DPM bottoms to reduce the DPM content to 5 wt. %. Comparative Frother F is also made from DPM bottoms, but is only propoxylated enough to reduce the DPM content to 17 wt. %.

TABLE 2

Froth Test Results: Frother E versus Comparative Frothers

| | | Froth stabililty[1] ranking | | Froth breakdown[2] ranking | | | Overall |
|---|---|---|---|---|---|---|---|
| Ex. # | Frother | Coarse | Fine | Coarse | Fine | Score | rank |
| 5 | E | 2 | 2 | 4 | 1 | 9 | 1 |
| C6 | B | 3 | 4 | 1 | 3 | 11 | 2 |
| C7 | F | 5 | 1 | 2 | 4 | 12 | T3 |
| C8 | C | 1 | 3 | 3 | 5 | 12 | T3 |
| C9 | D | 4 | 5 | 5 | 2 | 16 | 5 |

Frothers:
B = frother made as in Comp. Ex. B;
C = DowFroth 250;
D = TPM;
E = frother made as in Ex. E;
F = frother made as in Comp. Ex. F

[1]Froth stability: measures whether a stable froth can be generated (more stable is higher rank)

[2]Froth breakdown: measures how easily the froth separates from the ore (faster is higher rank)

As shown in Table 2, Frother E outperforms commercial frothers C and D. Its overall performance also exceeds that of Frother F, which is similarly produced from DPM bottoms but has a higher DPM content (17 wt. %). Frother B comes closest to meeting the overall performance of Frother E. However, Frother B requires relatively pure DPM to start and a vacuum distillation step to reduce the DPM level while Frother E is prepared from a bottoms stream without the need for such a distillation. Thus, Frother E is more convenient to prepare.

The preceding examples are meant only as illustrations. The following claims define the invention.

We claim:

1. A process which comprises:

(a) extracting a distillation residue comprising DPM, TPM, and at least 5 wt. % of a basic catalyst with water under conditions effective to provide an extracted residue comprising DPM, TPM, less than 15 wt. % of water, and less than 1 wt. % of the basic catalyst; and (b) reacting the extracted residue from step (a) with propylene oxide in an amount effective to produce a glycol ether composition comprising 4 to 15 wt. % of DPM, at least 20 wt. % of TPM, and one or more PO-based glycols.

2. The process of claim 1 wherein the PO-based glycols are selected from the group consisting of propylene glycol, dipropylene glycol, tripropylene glycol, and mixtures thereof.

3. The process of claim 1, wherein the DPM comprises one or more isomers.

4. The process of claim 1, wherein the DPM comprises ARCOSOLV® DPM.

5. The process of claim 1, wherein the basic catalyst comprises a catalyst selected from a group consisting of alkali metals, alkali metal hydroxides, alkali metal alkoxides, and double metal cyanide catalysts.

6. The process of claim 1, further comprising removing the basic catalyst prior to the extracting.

7. The process of claim 1, further comprising removing the basic catalyst, prior to the extracting, by water washing.

8. The process of claim 1, wherein the reacting comprises a temperature within a range of 50° C. and 200° C.

9. The process of claim 1, wherein the glycol ether composition is a frother.

* * * * *